United States Patent
Seay, III

[11] Patent Number: 6,126,623
[45] Date of Patent: Oct. 3, 2000

[54] SPLINT MEMBER AND METHOD OF USAGE

[76] Inventor: James Edward Seay, III, P.O. Box 690, 241 Smith St., Wingate, N.C. 28174

[21] Appl. No.: 09/289,293

[22] Filed: Apr. 9, 1999

[51] Int. Cl.⁷ ...................................................... A61F 5/00
[52] U.S. Cl. .................................................. 602/5; 602/12
[58] Field of Search ................................ 602/4, 5, 6, 12, 602/13, 15; 5/630, 636–648

[56] References Cited

U.S. PATENT DOCUMENTS

| | | | |
|---|---|---|---|
| 590,625 | 9/1897 | Paquette . | |
| 1,326,530 | 12/1919 | Radcliffe | 602/15 |
| 1,396,372 | 11/1921 | Kutwicz . | |
| 1,635,230 | 7/1927 | Spicer . | |
| 1,741,011 | 12/1929 | Carvill . | |
| 2,339,515 | 1/1944 | Parcher | 128/84 |
| 2,387,192 | 10/1945 | Straits | 602/12 |
| 2,486,687 | 11/1949 | Svaetichin | 128/88 |
| 3,256,880 | 6/1966 | Cayeinar | 128/133 |
| 3,624,745 | 11/1971 | Bower | 128/93 |
| 3,719,187 | 3/1973 | Ulansey | 128/90 |
| 3,745,997 | 7/1973 | Gledhill | 128/88 |
| 4,019,504 | 4/1977 | Sterling | 128/88 |
| 4,169,467 | 10/1979 | Rabischong | 602/13 |
| 4,383,526 | 5/1983 | Robins | 602/15 |
| 4,699,130 | 10/1987 | Hossler | 128/89 |
| 4,787,405 | 11/1988 | Karwoski | 135/66 |
| 5,101,815 | 4/1992 | Langdon-Orr et al. | 602/12 |
| 5,385,534 | 1/1995 | Cassford | 602/15 |
| 5,591,121 | 1/1997 | Cantrel | 602/5 |

*Primary Examiner*—Michael A. Brown

[57] ABSTRACT

A splint member comprises a rigid, elongated tube and a cushioning sleeve removably mounted to its exterior. The tube has an externally threaded and an internally threaded section, located on opposing ends of the tube. These threaded sections allow a splint member to be connected to another splint member, in an end to end fashion. The tube has a second internally threaded section, located at its midpoint. The second internally threaded section, allows for a splint member to be connected at a right angle to another splint member. The splint member may be fitted with connectors that allow it to be adjacently joined along its long axis to another splint member. By combining splint members, to increase length or width, a care giver can selectively assemble multiple types of devices for the temporary treatment of skeletal injuries.

17 Claims, 9 Drawing Sheets

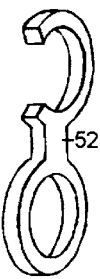
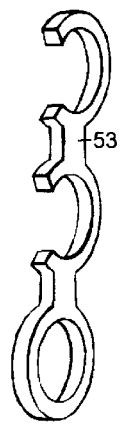
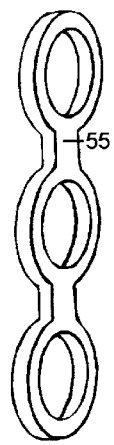
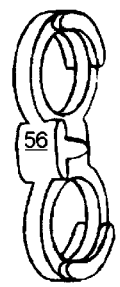
Fig. 3A  Fig. 3C  Fig. 3E  Fig. 3G
Fig. 3B  Fig. 3D  Fig. 3F
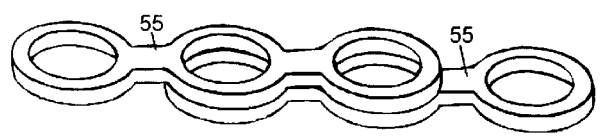
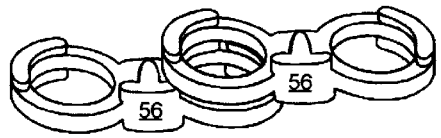
Fig. 3H  Fig. 3I
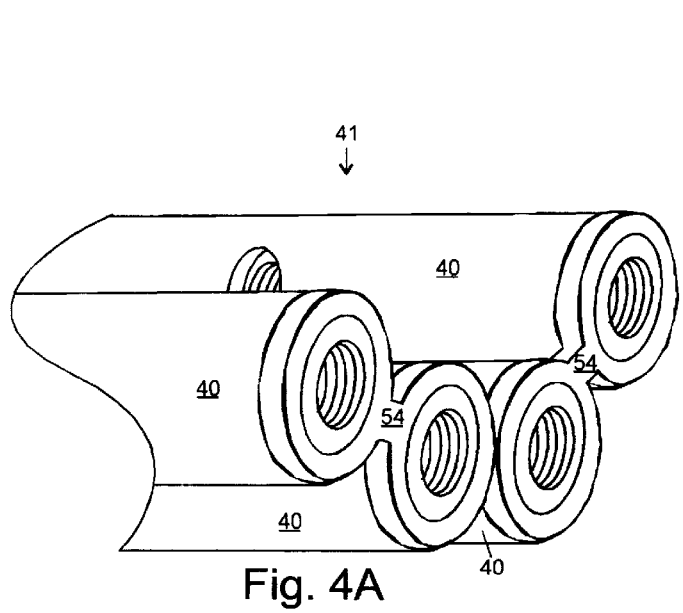
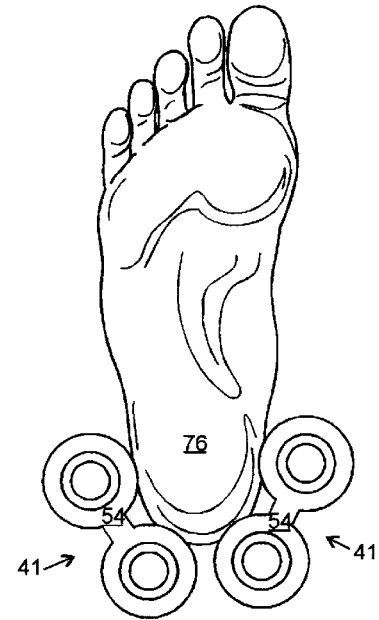
Fig. 4A  Fig. 4B

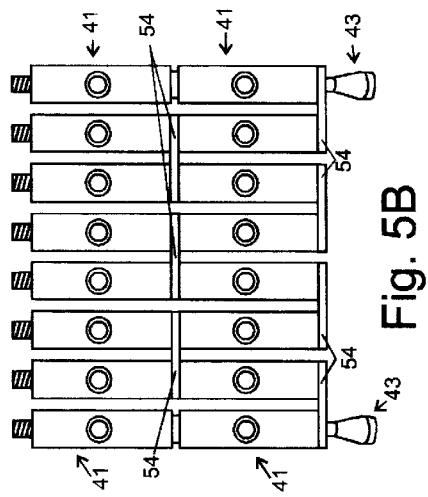
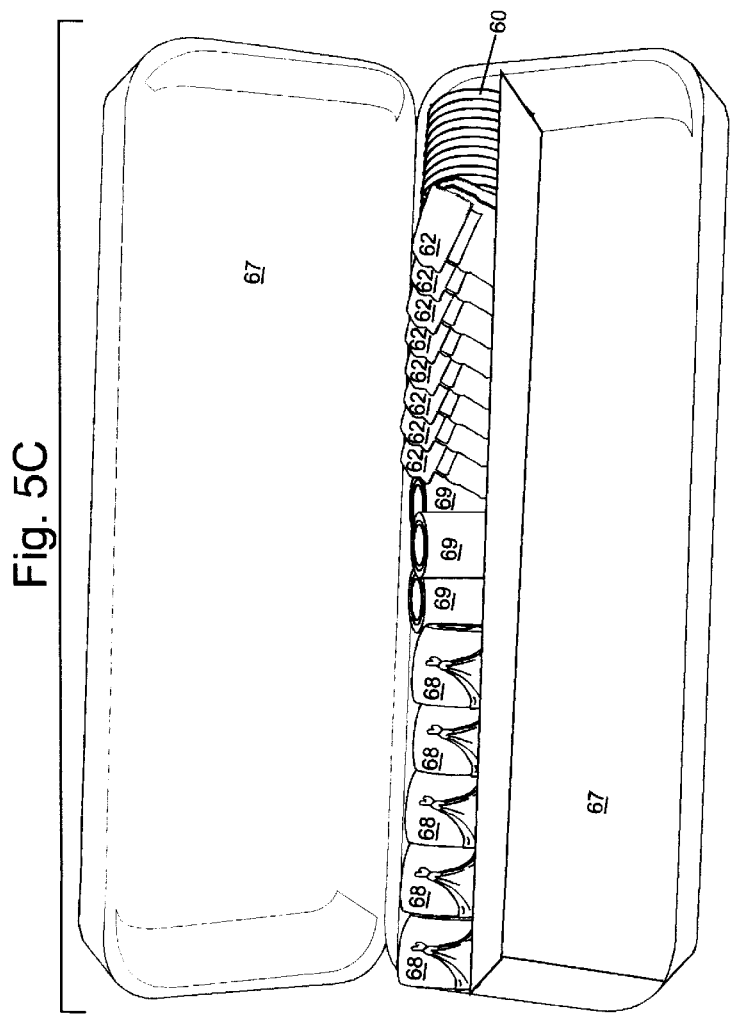
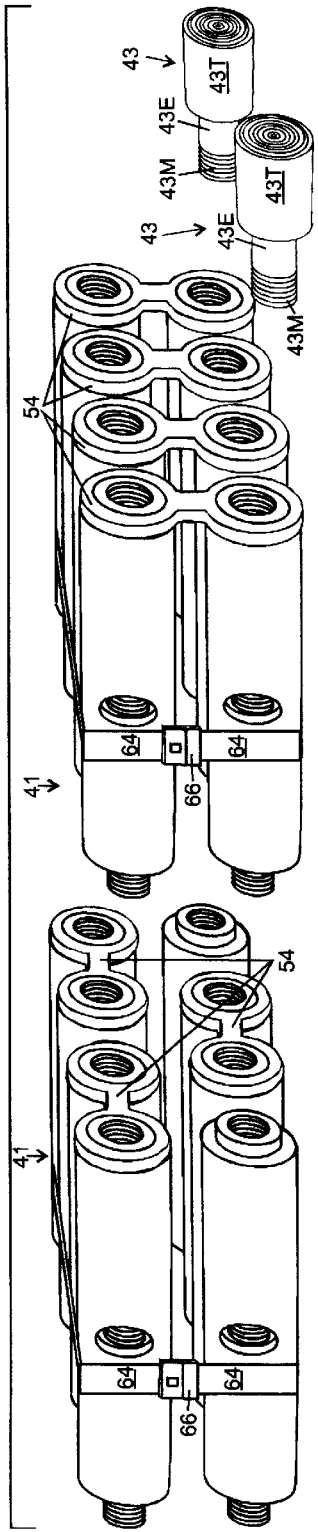

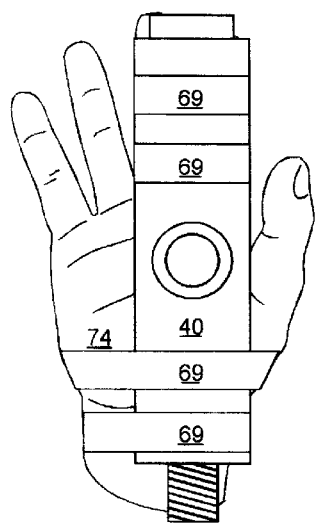
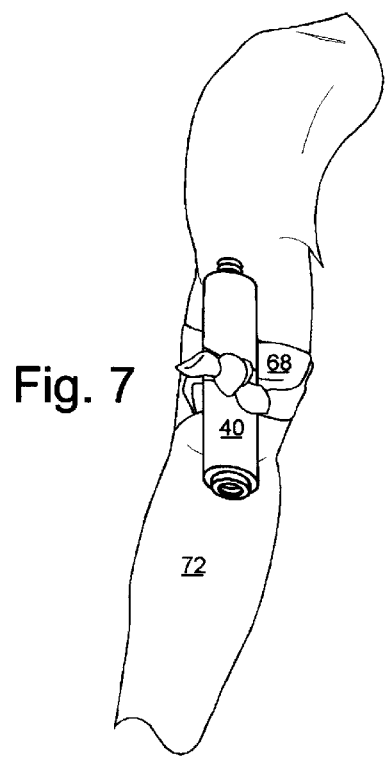
Fig. 6
Fig. 7
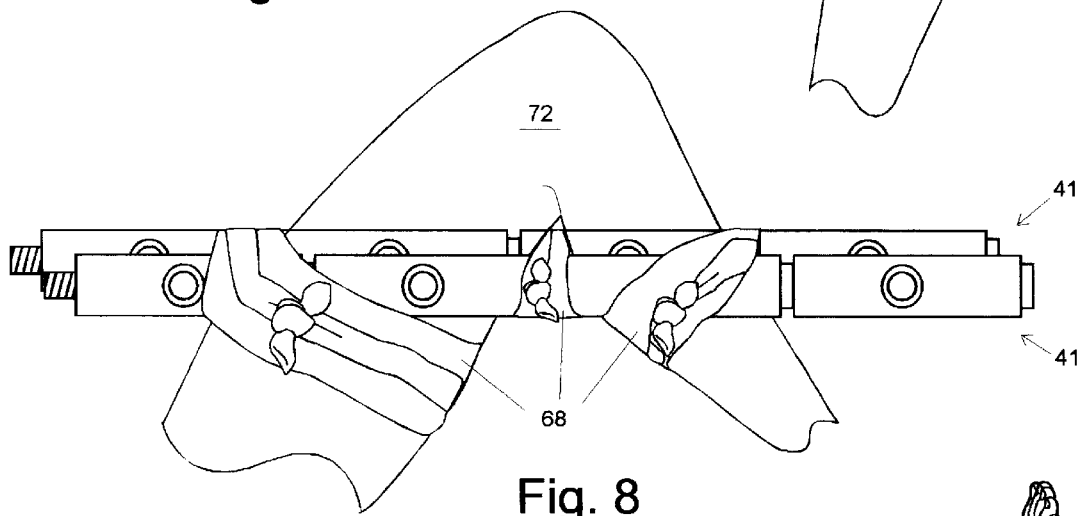
Fig. 8
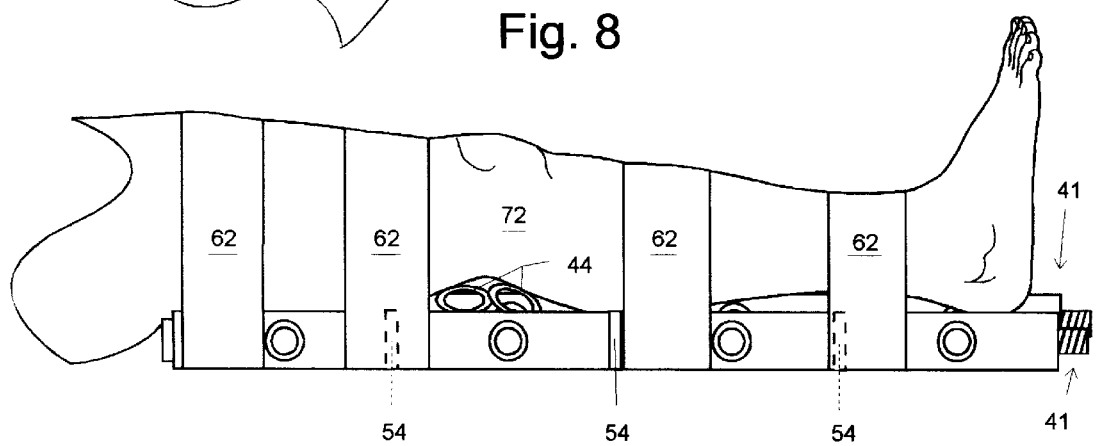
Fig. 9

SPLINT MEMBER AND METHOD OF USAGE

BACKGROUND

1. Field of the Invention

The present invention relates to the field of medical equipment, particularly to splints, and more particularly to a modular or sectional splint member which can be used independently or in combination for emergency treatment of skeletal injuries.

2. Discussion of Prior Art

Civilian first responders, emergency medical technicians, paramedics, and military field medical technicians commonly provide emergency treatment of skeletal injuries. These personnel are called upon to temporarily treat bone and joint injuries, that may range from a mild ankle sprain to a severe fracture of the femur. The aforementioned injuries would possibly be treated with a crutch and a traction providing splint, respectively.

These care givers currently select from a variety of treatment devices. These devices are generally limited to only a few applications. Therefore, care givers must have a means for the storage and transport of several different treatment devices. Care givers that use a rescue vehicle have allotted space for crutches, press boards for cardiopulmonary resuscitation, board splints, padding, back and spine boards, and traction providing devices. However, care providers that operate in remote, restricted access, or non-vehicle accessible areas don't have the ability, nor resources to carry all of these treatment devices.

Therefore, patients in remote locations may have a compromise in the quality of emergency care that is rendered. In addition, proper treatment of a severe injury may be delayed due to the absence of specialized equipment, such as a traction providing splint. This delay may cause further harm to a patient, such as the prolonged internal bleeding associated with an unstabilized femur fracture.

Inventors have created many types of splints, braces, and crutches. However, a majority of these devices are limited to a specific type of injury. Also present in the prior art, are devices having a modular or sectional characteristic that allow them to be more versatile. Several modular or sectional devices have been proposed—for example U.S. Pat. No. 590,625 to N. Paquette (1897), No. 1,326,530 to A. Radcliffe (1919), No. 1,396,372 to F. Kutwicz (1921), No. 1,635,230 to Spicer (1927), No. 1,741,011 to C. Carvill (1929), No. 2,387,192 to L. Straits (1945), No. 2,339,515 to A. Parcher (1944), No. 2,486,687 to G. Svaetichin (1949), No. 3,256,880 to E. Caypinar (1966), No. 3,624,745 to D. Bowers (1971), No. 3,719,187 to J. Ulansey (1973), No. 3,745,997 to W. Gledhill (1973), No. 4,019,504 to R. Sterling (1977), No. 4,169,467 to Rabischong et al. (1979), No. 4,383,526 to S. Robins (1983), No. 4,699,130 to P. Hossler (1987), No. 4,787,405 to D. Karwoski (1988), No. 5,101,815 to Langdon-Orr et al. (1992), No. 5,385,534 to K. Cassford (1995), and No. 5,591,121 to M. Cantrell (1997). Although capable of use with certain skeletal injuries, such devices are incapable of supporting a wide spectrum of emergency care needs. Thus, to temporarily treat a variety of skeletal injuries, care givers must have multiple treatment devices with them or treat the injuries in makeshift fashion with the available supplies.

Therefore, prior art designs for modular or sectional splints, traction providing splints, braces, and crutches heretofore known suffer from a number of disadvantages:

(a) Comfort of the patient is compromised for function. A majority of the prior art devices have no padding. Therefore injuries may be compounded by irritation at friction points.

(b) Traction providing capabilities aren't available with the design of many of the prior art samples. In addition, some of the materials used in several of the preferred embodiments wouldn't be able to support the tension produced by a traction device.

(c) Higher manufacturing cost are associated with the devices that have a traction applying capability. This increased production cost, resulting from the tooling needed for a winding mechanism, inflates the final product's price.

(d) A more complicated manufacturing process is incurred, due to each module or section not being of a single, simple design. Therefore, a mold would need to be manufactured, maintained, and stored for each of the different components.

(e) Several prior art devices are cumbersome and time consuming to use. This resulting from the use of small pieces, such as nuts and bolts, that need to be repositioned. The loss of just one piece would jeopardize the function of the device and possibly render it inoperative.

(f) Many prior art devices limit their usage to one type of injury. Therefore, they don't provide care givers with ample options, for the proper care of other types of injuries.

(g) Several prior art modular or sectional devices have individual parts that connect to only one or at most only a few other parts, typically in a specific order. If this order is not kept or a section is damaged, the entire device is rendered inoperative.

h) Several prior art devices are of a size that only a vehicle supported care giver could use them. By lacking a compact design, the universal application of these devices is restricted.

OBJECTS AND ADVANTAGES

Accordingly, several objects and advantages of the present invention are:

(a) to provide a splint member which is comfortable when affixed to an injured patient, as to not aggravate the existing injury nor to create any further injuries at friction points;

(b) to provide a splint member whose structural integrity is sufficient to support the tension produced by a traction device;

(c) to provide a splint member, in combination with other identical splint members, which can provide traction for an injured limb;

(d) to provide a splint member which has a simple cost effective design;

(e) to provide a splint member which is easy to assemble and use, even in low light or low visibility conditions;

(f) to provide a splint member, in combination with identical splint members, which will allow for the treatment of a wide range of skeletal injuries;

(g) to provide a splint member, in combination with identical splint members, which is not restricted to a single specific order of assembly;

(h) to provide a splint member which is compact and lightweight.

Further objects and advantages are to provide a splint member that is conveniently mass produced as to make it available to a wider range of care givers, which can be supplied in individual or multiple member kits, which is durable, which can be replaced inexpensively, which is washable, and which can be produced in different colors.

Further objects and advantages of the invention will become apparent from a consideration of the ensuing description and drawings.

DRAWING FIGURES

In the drawings, closely related figures have the same number but different alphabetic suffixes.

FIGS. 3A to 3I show various embodiments of splint member connectors.

FIGS. 4A and 4B show various aspects of multiple splint members, assembled to partially encompass the circumference of a limb.

FIGS. 5A to 5C show various aspects of a kit made from multiple splint members.

FIG. 6 is an orthogonal view of a splint member used to immobilize a finger.

FIG. 7 is a perspective view of a splint member used as a tourniquet handle.

FIG. 8 is an orthogonal view of multiple splint members, assembled to immobilize a bent limb.

FIG. 9 is an orthogonal view of multiple splint members, assembled to immobilize a straight limb.

Figure 1A:
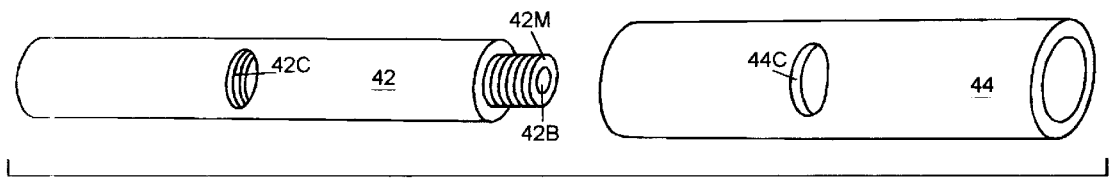
FIGS. 1A to 1E show various aspects the splint member of this invention.

REFERENCE NUMERALS IN DRAWINGS 40 splint member
41 multiple splint members
42 tubular element
42B bore of tubular element
42C internally threaded section
42F internally threaded section
42M externally threaded section
43 walker tipped member
43E short tubular extension
43M externally threaded section
43T rubber walker tip
44 cushioning sleeve
44C cutout in cushioning sleeve
50 figure three shaped connector
51 modified figure three shaped connector
52 figure six shaped connector
53 modified figure six shaped connector
54 figure eight shaped connector
55 modified figure eight shaped connector
56 interlockable eight shaped connector
60 nylon line
62 elastic strap
64 nylon strap
66 quick release buckle
67 case
68 bandage
69 medical tape
70 injured patient
72 injured limb
74 injured hand
76 injured foot
78 care giver
80 paddle head attachment
82 tent
84 tent stake
86 coat

SUMMARY

In accordance with the present invention a rigid, elongated splint member for the temporary treatment of skeletal injuries. The splint member comprises a tubular element, with a cushioning sleeve removably mounted to it exterior. The splint member can be joined in an end to end or a side by side fashion. In addition, a splint member can be joined perpendicularly to another splint member. Thus, allowing for the assembly of emergency treatment devices for multiple types of skeletal injuries.

FIGS. 1 and 2

Detailed Description of the Splint Member

Figure 1B:
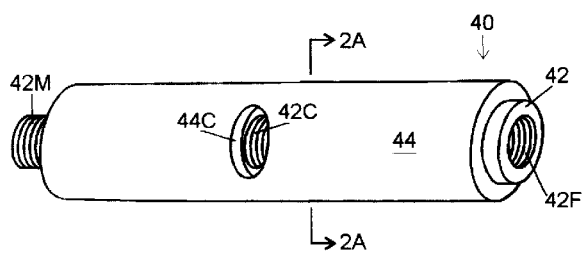
Figure 1C:
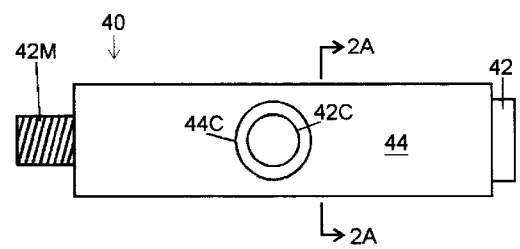
Figure 1D:
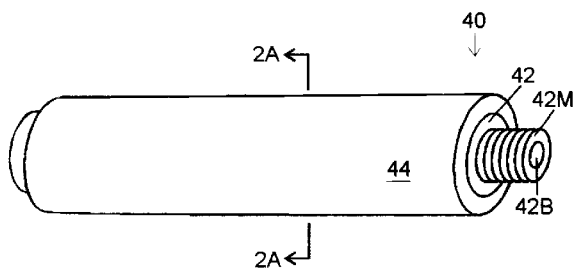
Figure 1E:
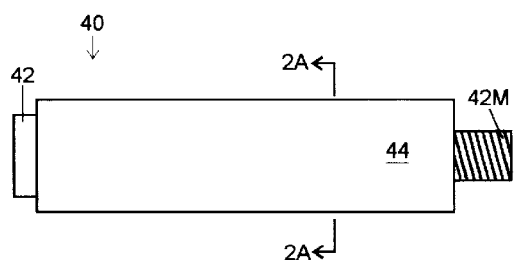
Figure 2A:
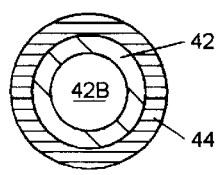
FIGS. 2A to 2C show cross-sectional views of several embodiments of the splint member.
Figure 2B:
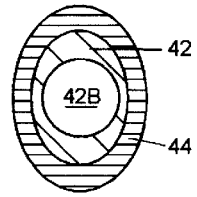
Figure 2C:
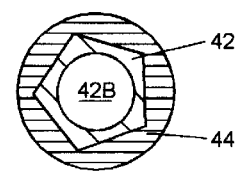

A splint member according to the invention is shown in the attached drawings, wherein FIGS. 1A, 1B, and 1D are perspective views of the splint member, FIGS. 1C and 1E are orthogonal views of the splint member, and FIGS. 2A, 2B, and 2C are cross sectional views of the splint member. The splint member 40 comprises an elongated tubular element 42 of uniform cross section consisting of a substantially rigid material. A cushioning sleeve 44 is placed around the exterior of the tube. In the preferred embodiment, the tubular element is hollow and made of a lightweight metal or alloy, such as aluminum. However, the tubular element can consist of any other materials that is of suitable strength, such as steel, magnesium, wood, plastic, composite materials, etc. Also in the preferred embodiment, the cushioning sleeve 44 is made of a closed cell resilient foam material, such as polyurethane foam. However, the cushioning sleeve 44 can consist of any other material, open or closed cell, that is of suitable padding thickness, such as fabric, foam rubber, foam plastic, neoprene foam, vinylnitril foam, etc.

The tubular element has at one end an internally threaded section 42F and at the other end an externally threaded section 42M. The ends of the tubular element 42 are of dimensions that allow them to be threadily mated. The tubular element 42 has a second internally threaded section 42C, positioned near the midpoint and orientated perpendicular to the long axis. The second internally threaded section 42C is of a dimension that allows the externally threaded end 42M to be threadily mated. The cushioning sleeve 44 is of an elongated tubular shape that is of a diameter that allows for a snug fit onto the exterior of the tubular element. The cushioning sleeve 44 has a cutout 44C located near its midpoint, that corresponds to the second internally threaded section 42C of the tubular element. The cushioning sleeve 44 advances onto the tubular element from either end. FIG. 2A shows a cross sectional view of the preferred embodiment of the splint member. FIGS. 2B and 2C show cross sectional views of a second and third embodiment of the splint member.

The tubular element has an overall length roughly from 8 inches to 12 inches, a diameter from ½ inch to 1½ inches, and a wall thickness from roughly ⅛ inch to ¼ inch. The cushioning sleeve 44 has roughly an overall length from 7 inches to 12 inches, a diameter from ½ inch to 1½ inches, and a wall thickness from roughly ⅛ inch to ½ inch.

FIGS. 3 and 4

Detailed Description of Splint Member Connectors

The splint member 40 of the invention can be joined, in a side by side position, with another splint member 40. FIGS. 3A, 3B, 3C, 3D, 3E, 3F, and 3G are perspective views of various embodiments of splint member connectors. The term splint member connectors will simply refer to the group as a whole, since they each perform the same basic function. FIGS. 3H and 3I show the splint members connectors positioned to lock the multiple splint members into a flat, board-like position and FIGS. 4A and 4B show various aspects of how these splint member connectors allow the multiple splint members 41 to partially encompass the circumference of a limb.

FIG. 3A shows a FIG. 3 shaped connector 50; FIG. 3B shows a modified FIG. 3 shaped connector 51; FIG. 3C shows a FIG. 6 shaped connector 52; FIG. 3D shows a modified FIG. 6 shaped connector 53; FIG. 3E shows a FIG. 8 shaped connector 54; FIG. 3F shows a modified FIG. 8 shaped connector 55; FIG. 3G shows an interlockable FIG. 8 shaped connector 56. In the preferred embodiment, the splint member connectors are solid throughout their cross section and made of a lightweight metal or alloy, such as aluminum. However, the splint member connectors can consist of any other materials that is of suitable strength, such as steel, magnesium, wood, plastic, composite materials, etc.

Each splint member connector engages the exterior surface of at least two tubular elements 42. The tubular element 42 circumference may be engaged partially or completely. The splint member connectors that partially engage the tubular element 42 will snap into position, while the completely engaging connectors must be slid into position from either end of the tubular element.

The splint member connectors that engage only two tubular element are roughly ¼ inch to ½ inch in thickness, 3 inches to 5 inches in overall length, the inner wall of the opening is slightly greater in diameter than the tubular element 42 it engages, and the diameter of the outer wall of the opening is roughly ⅛ inch to ½ inch greater than the inner wall diameter. The splint member connectors that engage more that two tubular elements 42 are proportionally greater in overall length, by roughly 1½ inches to 2½ inches per additional tubular element 42 engaged.

FIG. 5

Detailed Description of a Splint Member Kit

There are various possibilities with regard to how several splint members 40 and splint member connectors may be assembled to form a kit. The preferred embodiment of a kit, as illustrated in FIGS. 5A and 5B, includes 16 splint members 40 and 7 connectors 54, with two walker tipped members 43, and held in form by two 1 inch wide nylon straps 64 with quick release buckles 66.

An additional kit embodiment is shown in FIG. 5C, which illustrates a case 67 that can hold nylon line 60, elastic straps 62, bandages 68, and medical tape 69 for attaching the splint members 40 to an injured patient.

FIGS. 6 and 7

Description of Injuries Treatable with a Splint Member

Several skeletal injuries are temporarily treated with the splint member 40. FIG. 6 shows a finger that has experienced a dislocation or suspected fracture. FIG. 7 show a limb that has experienced a traumatic amputation.

FIGS. 8, 9, 10, 11, 12, 13 and 15

Description of Injuries Treatable with a Splint Member Kit

Figure 10A:
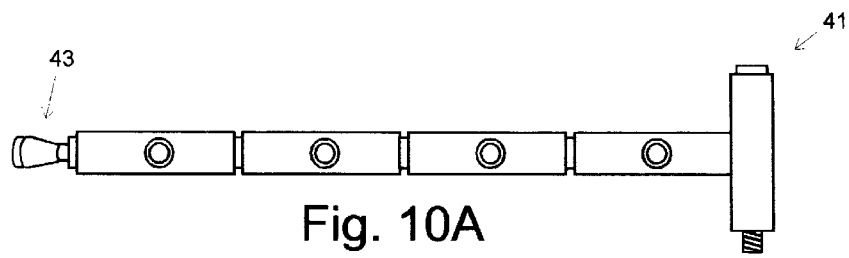
FIGS. 10A and 10B show various aspects of multiple splint members, assembled as walking aids.
Figure 10B:
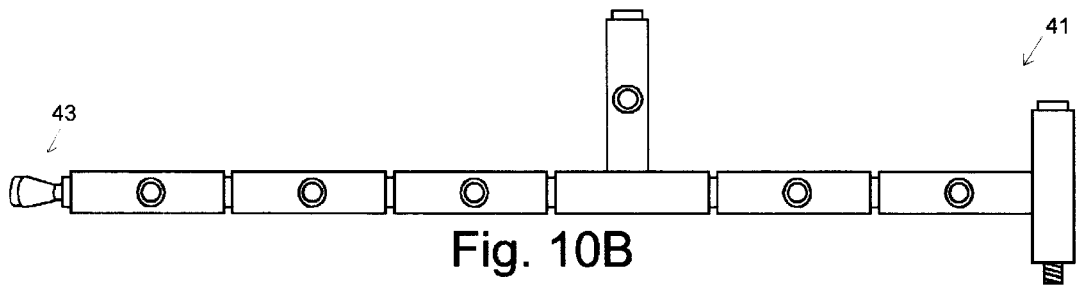
Figure 12:
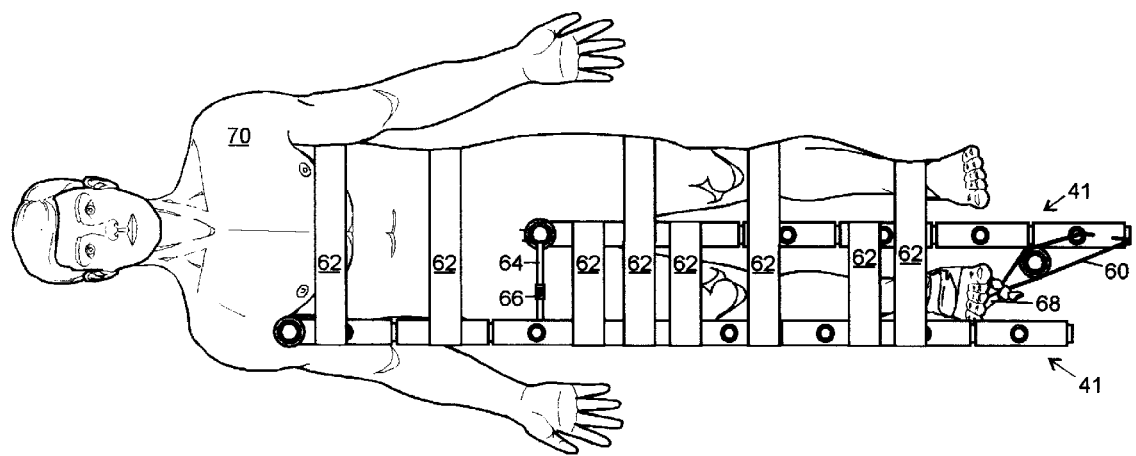
FIG. 12 is an orthogonal view of multiple splint members, assembled to immobilize a hip injury.
Figure 13:
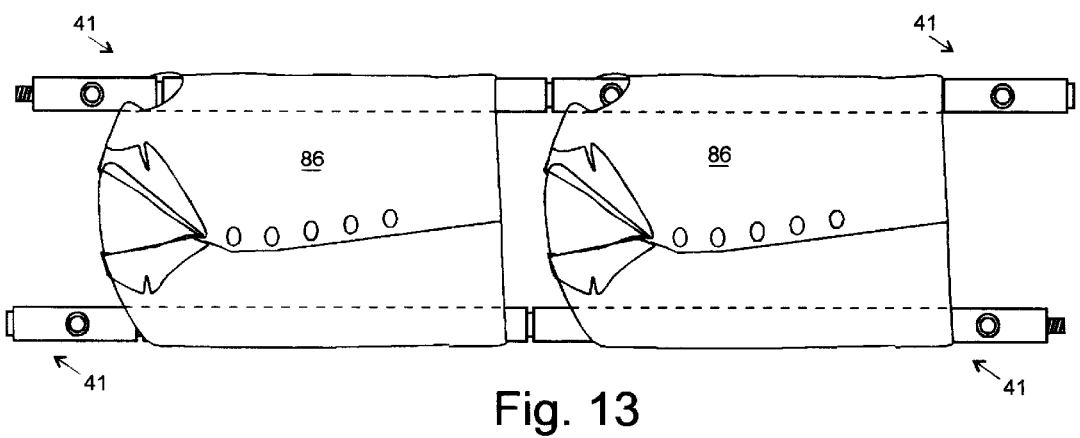
FIG. 13 is an orthogonal view of multiple splint members, assembled to carry a patient.
Figure 15:
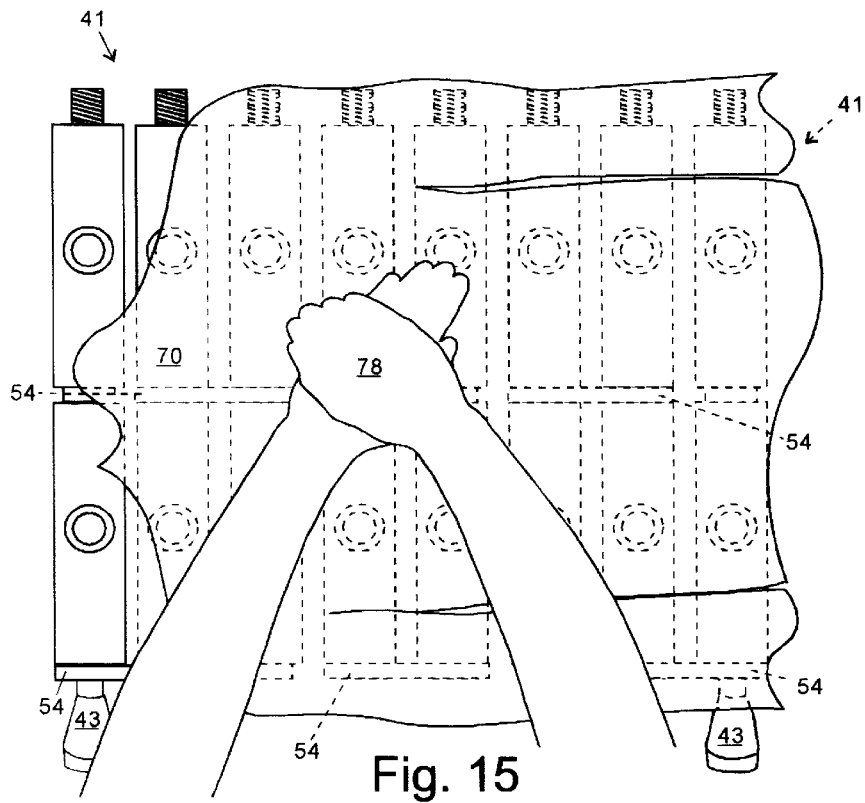
FIG. 15 is an orthogonal view of a kit used as a cardiopulmonary pulmonary resuscitation press board.

Multiple skeletal injuries are temporarily treated with a kit. FIG. 8 shows an injured limb 73, such as an arm or leg, that required immobilization in a bent position. FIG. 9 shows and injured limb 72, such as an arm or leg, that required immobilization in a straight or slightly bent position. FIGS. 10A and 10B show walking aids to assist a patient in ambulation. FIGS. 11A, 11B, 11C, and 11D show and injured limb, such as a suspected femur fracture, that requires traction. FIG. 12 shows a patient that has experienced a hip dislocation or suspected fracture. FIG. 13 shows a stretcher to transport a patient upon. FIG. 15 shows a patient receiving cardiopulmonary resuscitation, with a kit acting as a press board.

FIG. 14

Description of Injuries Treatable with Several Splint Member Kits

Figure 14A:
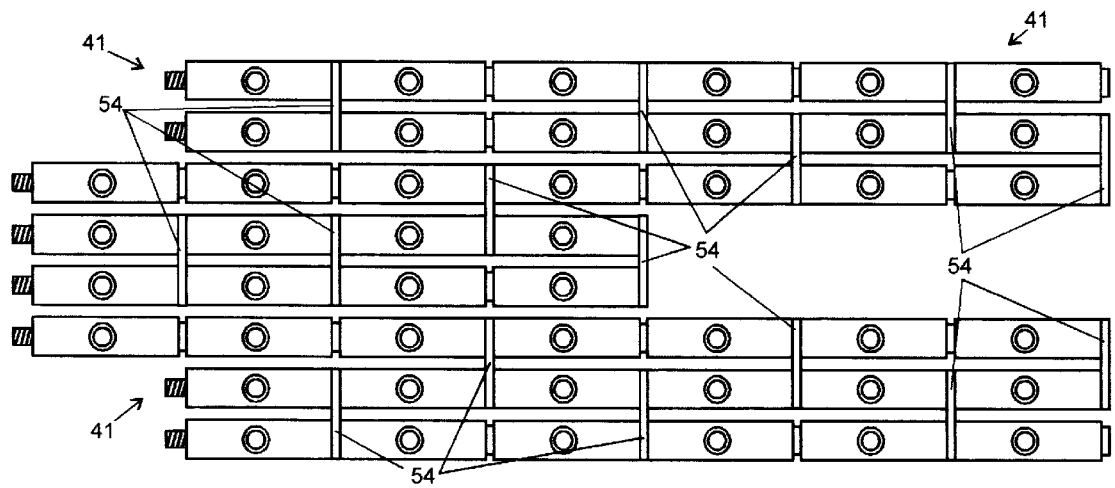
FIGS. 14A and 14B show various aspects of multiple splint members, assembled to immobilized a patient.
Figure 14B:
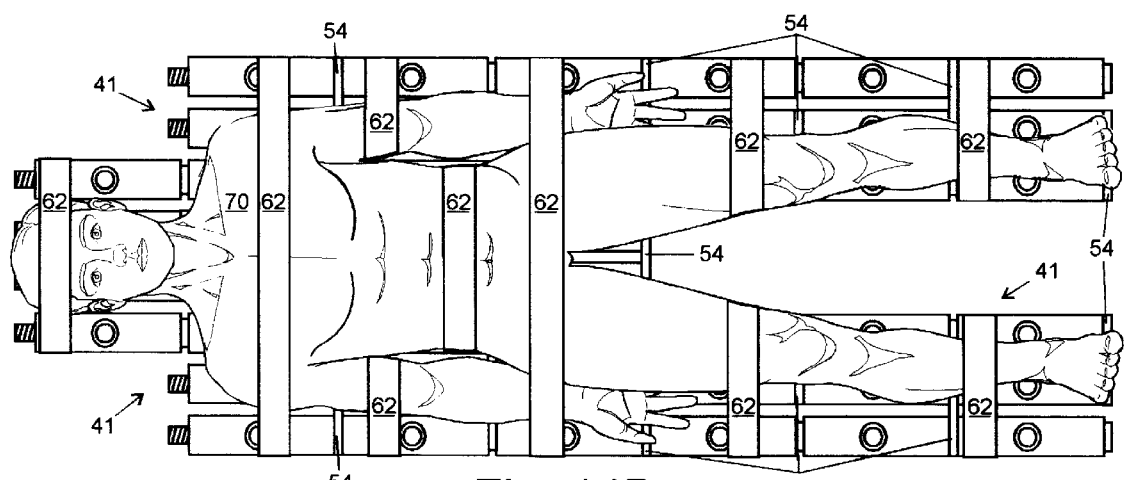

When several kits are available to a care giver, multiple injuries can be treated at once. FIG. 14B shows a patient that has experienced unconsciousness, head trauma, suspected cervical injury, suspected spinal injury, severe multiple injuries, or who has received medication that doesn't allow ambulation.

FIG. 16

Description of Alternative Applications for Multiple Splint Members

Figure 16A:
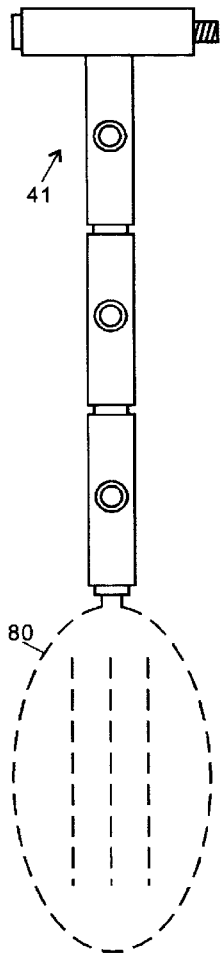
FIGS. 16A and 16B show various aspects of alternate uses for the splint member.
Figure 16B:
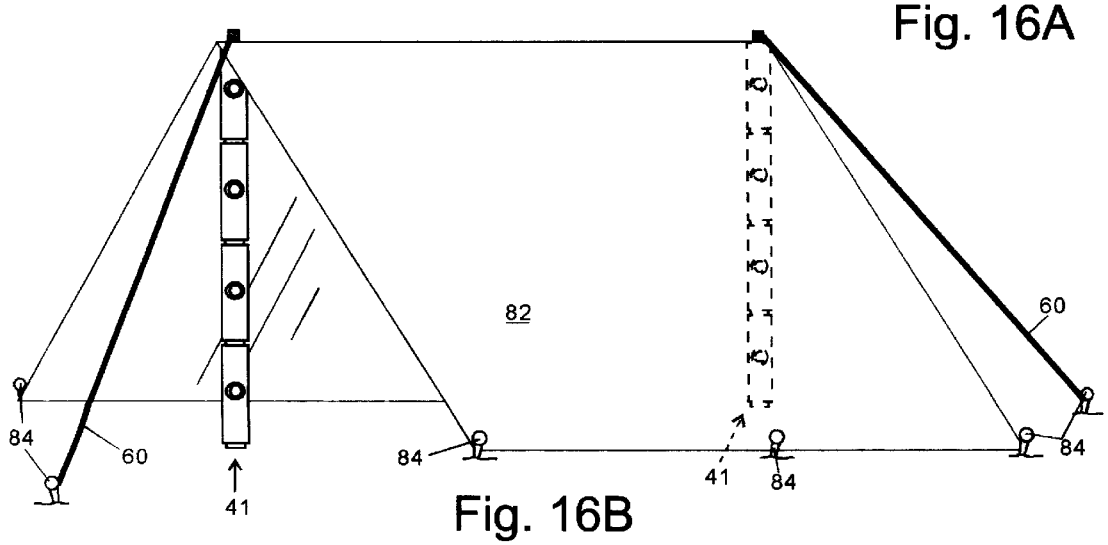

Several alternate applications for multiple splint members 41 are illustrated by FIGS. 16A and 16B. FIG. 16A show a compact, lightweight, paddle 80 for use in an emergency life raft. FIG. 16B shows multiple splint members 41 assembled to support a tent 82 or military shelter-half.

From the description above, a number of advantages of my splint member become evident:

(a) It provides sufficient rigidity to immobilize an injury and still provide cushioning to eliminate further injury to tender tissue, bones, and joints.

(b) When assembled to provide traction on an injured limb, the structural integrity is sufficient to support the tension produced by the application of traction.

(c) It has a single simple design, thus allowing easy and cost effective mass production.

(d) Each splint member is identical, so it is simple to assemble and easy to use.

(e) Because each splint member, of a kit, is the same a care giver can assemble the members by feel, even in low light or low visibility conditions.

(f) Because of the simple design a care giver is provided with a tool to treat multiple types of injuries, all from one kit.

(g) By having multiple identical splint members in a kit, one lost or damaged splint member doesn't interfere with the quality of treatment a care giver can provide.

(h) With a compact and lightweight design, an individual can easily carry several splint members at one time. In addition, a group of hikers, rafters, or soldiers can each carry several splint members each, which would be collected and assembled to treat an injured person.

FIGS. 1, 6, and 7

Operation of the Splint Member

The manner of providing emergency treatment of skeletal injuries with the splint members and connectors is identical to that care in present use. Currently a care giver would select the appropriate splint device, such as a board splint, traction device, or a backboard. Next, the care giver would place the selected device adjacent to the injured arm, leg, or patient. Lastly, the care provider would secure the selected device to that arm, leg, or patient with medical tape, bandages, straps, etc. While stabilizing the injured area, the care giver is continually monitoring the patient's status, such as their airway, breathing, circulation, neurological function, etc. However, with the splint members and connectors of this invention, the care giver would simply assemble a splint, traction device, or backboard.

FIG. 1A shows that the tubular element 42 and cushioning sleeve 44 can be separated, this may be necessary in several situations. For example, a care giver may need to pad a void to build up support between a splint member and the injured limb. By removing the cushioning sleeves 44 of unused splint members 40 or splint members that are not in contact with the patient, the rescuer has additional padding readily available. Secondly, a cushioning sleeve 44 may become worn or torn and need to be replaced. Thirdly, a splint member 40 may be soiled with dirt, oil, fecal matter, urine, or blood so the tubular element 42 would need to be cleaned and the cushioning sleeve 44 replaced. Fourthly, a care giver may desire to change the color of the splint member 40. This can be done easily by replacing the cushioning sleeve with a camouflaged or colored sleeve. Lastly, a closed cell foam cushioning sleeve would keep fluid out, but may need to be replaced with an open cell foam if the care giver operates in a hyperbaric or hypobaric environment. Because the changing ambient pressure, as the patient return to sea level, could decrease the snug support of the splint member or increase pressure on the injured limb. Even with the cushioning sleeve removed the tubular element 42 operates the same.

FIG. 6 shows an injured finger being immobilized with a splint member 40. The splint member 40 is held in place by medical tape 69. However, bandages, wraps, or other straps would secure it just as well. In this illustration two fingers are secured to give additional support to the injured finger.

FIG. 7 shows a splint member 40 being used as a tourniquet handle. This treatment is a last resort to slow or stop uncontrollable bleeding. The care giver would wrap a bandage 68 around the injured limb, secure the splint member 40 in the bandage, and turn it slowly until the desired result is reached. The care giver should follow local protocol when using the splint member in this manner.

FIGS. 8, 9, 10, 11, 12, 13, and 15

Operation of a Splint Member Kit

FIG. 8 show how multiple splint members 41 can be connected end to end. Then placed on each side of a bent limb. When immobilizing injuries the care giver attempt to splint the limb in the position found. As shown, bandages 68 are used to connect the splint members in three positions. However, wraps or other straps would secure it just as well. This three point securing method immobilizes the bones superior and inferior to the joint.

FIG. 9 shows multiple splint members 41 and eight shaped connectors 54 assemble to treat a straight or slightly bent limb. The care giver has used elastic straps 62 to secure the splint. The connectors 54 allow the splint member to fit in a snug manner around the injured limb. The void between the knee and the splint members has been padded with cushioning sleeves 44 from other splint members 40.

FIGS. 10A and 10B show multiple splint members 41 assembled as walking aids, they each have a walker tipped member 43 on their distal end. The cane, illustrated in FIG. 10A, has a horizontal splint member 40 positioned as a handle. The crutch, illustrated in FIG. 10B, has a upper horizontal splint member 40 to fit in the patient's arm pit (axillary area), and a lower horizontal splint member 40 to act as a handle. The handle will bear the majority of the patient's weight. Because the axillary area has many nerves, irritation may occur if a patient were to ride the upper horizontal splint member 40.

Figure 11D:
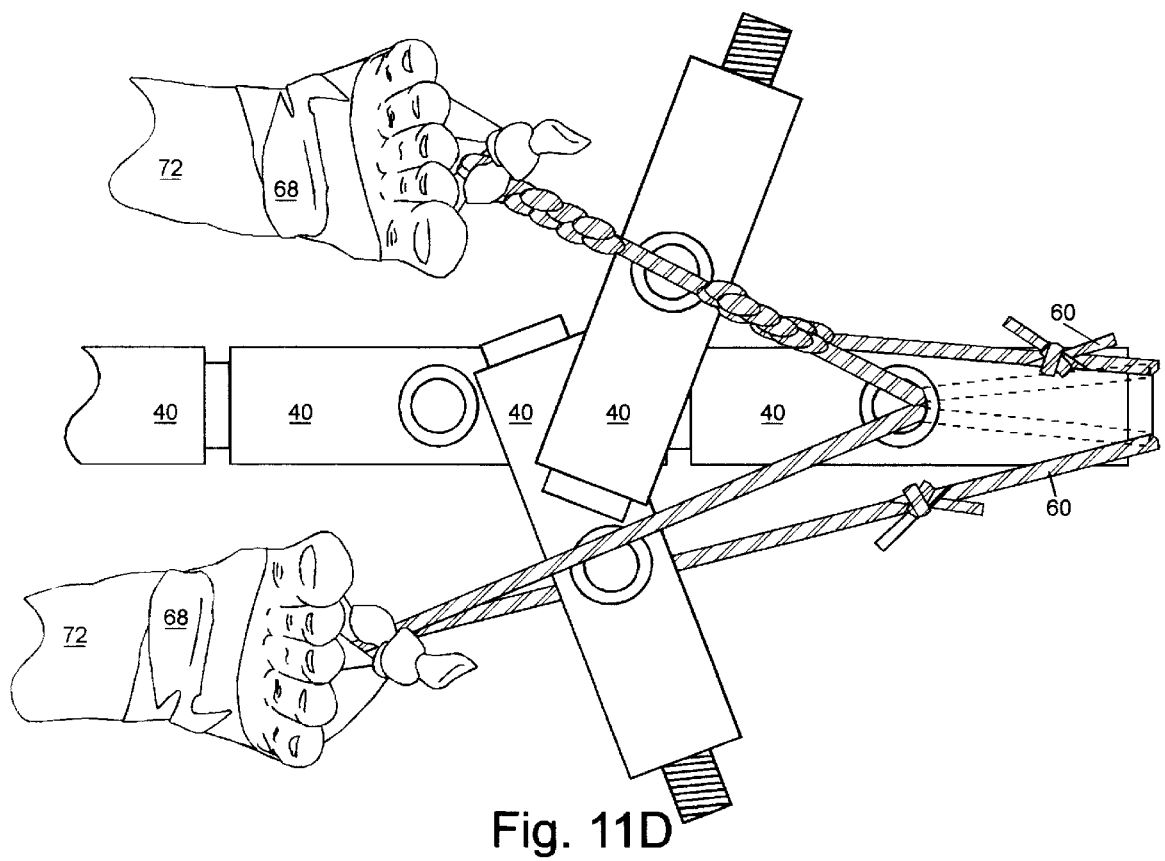
FIGS. 11A to 11D show various aspects of multiple splint members, assembled to provide traction.
Figure 11A:
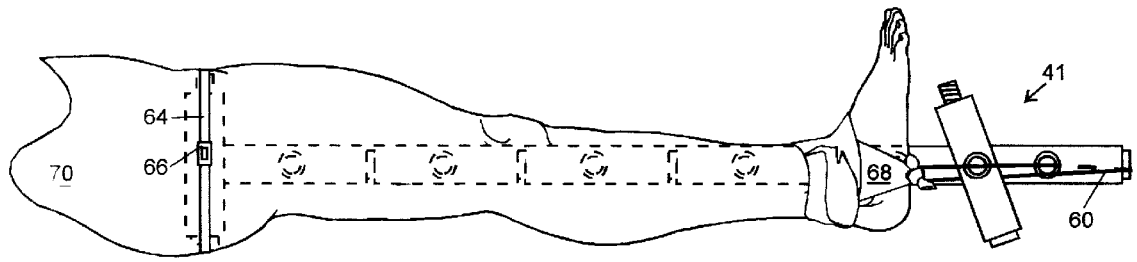
Figure 11B:
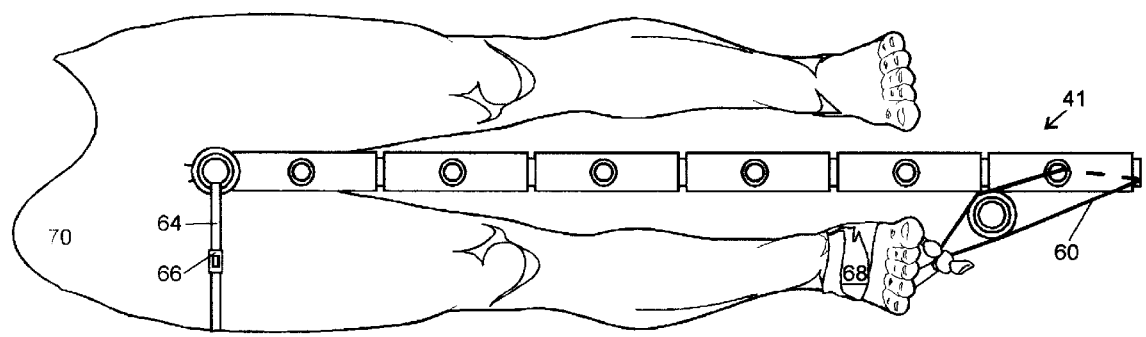
Figure 11C:
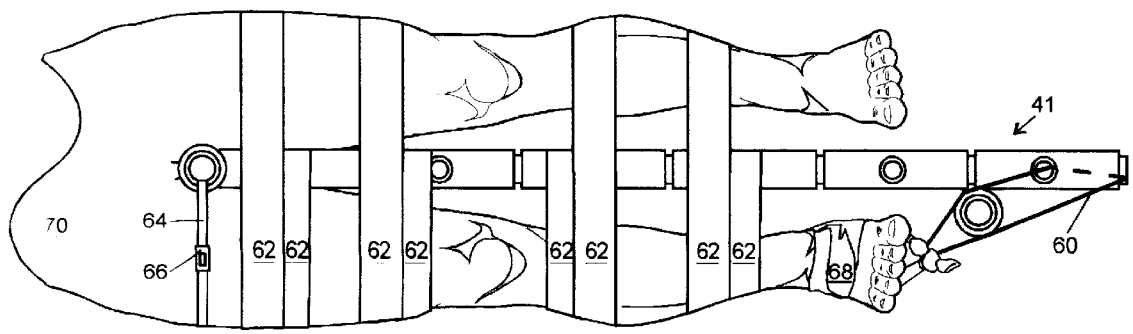

FIGS. 11A, 11B, 11C, and 11D show the steps taken to apply traction to an injured limb. FIGS. 11A and 11B show the assembled traction device and how it is to be positioned. A splint member 40 is placed perpendicular to the other splint members. This splint member is placed between the patient's legs and secured to the injured leg with a nylon strap 64 and quick release buckle 66. The foot of the injured limb is fitted with a bandage 68 or other ankle hitch (not shown). A nylon line 60 is threaded from the last splint member 40 back to the bandage 68 and secured with a knot. A second care giver is stabilizing the injured limb as multiple splint members 41 are arranged. FIG. 11D shows how a splint member 40 is placed within the loop of the nylon line 60 and then wound in a plane perpendicular to the nylon line. This winding force causes the nylon line to bunch up and shorten, thus pulling traction on the injured leg. Once the injured leg is the same length as the unaffected limb or when pain subsides for the patient the winding would be stopped. The care giver would follow local protocol on the amount of traction to provide. The splint member 40 would then be secured to the main splint member pole with medical tape 69, a strap 64, or additional nylon line 60, so that accidentally unwinding would be prevented. FIG. 11C shows how elastic straps 62 are used to secure multiple splint members 41 to the injured leg 72, and also to secure the injured leg to the unaffected leg. FIG. 11D shows how bilateral, independent traction can be achieved if a patient had suspected fractures of both femurs.

FIG. 12 shows how an injured hip would be immobilized. The assembly is similar to that of FIG. 11A, with the addition of another crutch like assembly placed laterally of the injured hip. The multiple splint members 41 are secured to the patient with elastic straps 62. The patient's legs are also secured with elastic straps. This configuration would allow for the application of traction if indicated or ordered by a physician.

FIG. 13 shows how a stretcher for transporting a patient would be assembled. The multiple splint members 41 are assembled into two poles. The sleeves of two coats 86, or heavy shirts, are turned outside in. Each coat 86 would then be buttoned or zipped closed. The poles are then passed through the sleeves. This arrangement would allow a non-ambulating patient to be moved.

FIG. 15 shows a care giver 78 providing cardiopulmonary resuscitation to a patient 70. If the patient was on a soft, flexing, or cushioned surface, the care giver's 78 compressions would be ineffective. By placing multiple splint members 41 under the patient, the care giver would then be able to increase the effectiveness of their compressions.

FIG. 14

Operation of Several Splint Member Kits

When multiple splint member 41 kits are available, or when several people are carrying a few splint members 40 each, large splints may be assembled. FIG. 14A shows multiple splint members 41 and connectors 54 assembled to form a backboard, litter, or stretcher. FIG. 14B show a patient 70 that has been completely immobilized with this backboard. The patient 70 is secured to the backboard with elastic straps 62. The backboard can be assembled to fit the circumference of the patient or it can be assembled to be a flat, board like structure. The use of different splint member connectors would allow the care giver to select which shape is best. The patient would then be transported on the formed backboard or be place on a poled litter, blanket, or cloth and carried by the care givers.

FIG. 16

Operation of Alternative Applications of the Splint Member

FIG. 16A shows how multiple splint members 41 may be integrated into a compact paddle. The cushioning sleeve 44 would provide additional positive buoyancy for the complete unit. The splint members would be assembled with a paddle head 80.

FIG. 16B shows how the splint member 40 may be assembled to form a pole. This pole would be used to hold up a tent 82. This embodiment would allow a collapsible tent pole that was lightweight and easily stored. Hikers, campers, military units, and rafters would be able to have several splint members 40 on hand at all times.

CONCLUSION, RAMIFICATIONS, AND SCOPE OF INVENTION

Accordingly, the reader will see that the splint member of this invention provides a highly reliable, compact, lightweight, comfortable, versatile, yet simple, and economical device that can be used by care givers at almost any level of training. Furthermore, the splint member 40 has the additional advantages in that It permits the production of cushioning sleeves in a variety of colors, allowing the manufacturer to target different market segments;

It provides a x-ray friendly device, when made from a material that is radiolucent. Thus not interfering with the diagnosis of injuries.

It provide a device that is easily incorporated into kits or packages as a handle, brace, pole, or support for other structures and devices.

Although the description above contains may specificities, these should not be constructed as limiting the scope of the invention but as merely providing illustrations of some of the presently preferred embodiments of this invention. For example, the tubular element can have other smaller or larger dimensions and other cross sectional shapes, such as triangular, square, rectangular, hourglass, etc.; the tubular element can be made of a different materials; the cushioning sleeve can be made of a different materials; the cushioning sleeve can be eliminated; the tubular element and cushioning sleeve can be integrated into one piece; the splint member connectors can be made of a different material; the tubular element can have more internally threaded sections at differing angles to the long axis, such as a 45 degree orientation to the long axis; the splint member connectors can have a different shape, such as oval, square, rectangular, etc.; the tubular element can be solid, such as a rod; the tubular elements can connect end to end by a different means, such as clasps, clips, hinges, hook and loop, interlocking joints, male to female joints, etc.

Thus the scope of the invention should be determined by the appended claims and their legal equivalents, rather than by the examples given.

What is claimed is:

1. In a modular splint member for stabilizing the joints and limbs of an injured human, comprising:
   (a) a tubular element of sufficiently rigid material of a predetermined size and length,
   (b) said tubular element having a predetermined cross sectional shape,
   (c) said tubular element having at least two ends,
   (d) said tubular element having joining means for connecting at least two substantially identical tubular elements directly end to end,
   (e) said tubular element having joining means for connecting at least one substantially identical tubular element approximately perpendicular thereof,
   (f) whereby a human can selectively assemble multiple modular splint members in various configurations for securing alongside different types of injuries.

2. The modular splint member of claim 1 wherein at least one said end having an externally threaded section.

3. The modular splint member of claim 1 wherein at least one said end having an internally threaded section.

4. The modular splint member of claim 1 wherein said tubular element having a cushioning means at least removably mounted to the exterior thereof.

5. The modular splint member of claim 1 wherein said tubular element having an elliptical cross sectional shape.

6. The modular splint member of claim 1 wherein said tubular element is constructed of an alloy material.

7. The modular splint member of claim 1 wherein said alloy material is aluminum.

8. The modular splint member of claim 1 wherein said tubular element is constructed of a plastic material.

9. The modular splint member of claim 1 wherein said tubular element is constructed of a composite material.

10. The modular splint member of claim 1 wherein said tubular element is constructed of metal.

11. In a traction device, comprising:
    (a) a plurity of substantially identical tubular elements,
    (b) said tubular element having a predetermined cross sectional shape, (c) said tubular elements having at least two ends, (d) said tubular element having joining means for connecting at least two substantially identical tubular elements directly end to end, (e) said tubular element having joining means for connecting at least one substantially identical tubular element approximately perpendicular thereof, (f) a traction force is resultant from a winding force such that the plane of rotation of said force is generally perpendicular to the long axis of the injured limb, (g) said winding force is not produced by a threaded screw like piece, (h) said winding force is produced by twisting said tubular element between at least two study lines, (i) said tubular element is not positioned at the distal end of the sturdy lines, (j) whereby a human can selectively assemble multiple modular splint members for providing tension on an injured limb.

12. The traction device of claim 11 wherein said tubular element for producing a winding force is position generally at the midpoint of said sturdy lines.

13. The modular splint member of claim 11 wherein said tubular element is constructed of an alloy material.

14. The modular splint member of claim 11 wherein said alloy material is aluminum.

15. The modular splint member of claim 11 wherein said tubular element is constructed of a plastic material.

16. The modular splint member of claim 14 wherein said tubular element is constructed of a composite material.

17. The modular splint member of claim 14 wherein said tubular element is constructed of metal.

* * * * *